(12) United States Patent
Elseviers et al.

(10) Patent No.: US 6,458,570 B1
(45) Date of Patent: Oct. 1, 2002

(54) PROCESS FOR THE PRODUCTION OF XYLITOL

(75) Inventors: Myriam Elseviers, Kampenhout; Harald Wilhelm Walter Röper, Brussels, both of (BE)

(73) Assignee: Cerestar Holding B.V., Sas Van Gent ( * ) Notice: Subject to any disclaimer, the term of this patent is extended or adjusted under 35 U.S.C. 154(b) by 0 days.

(21) Appl. No.: 08/680,139

(22) Filed: Jul. 15, 1996

(30) Foreign Application Priority Data

Jul. 15, 1995 (GB) ............................................. 9514538

(51) Int. Cl.$^7$ ............................... C12P 7/18; C12P 7/04; C12N 1/00; C12N 1/14
(52) U.S. Cl. ......................... 435/158; 435/155; 435/157; 435/921; 435/930; 435/938; 435/940; 435/944
(58) Field of Search ................................ 435/158, 157, 435/155, 921, 930, 938, 940, 944

(56) References Cited

U.S. PATENT DOCUMENTS

| | | | |
|---|---|---|---|
| 3,607,652 | * 9/1971 | Ueda | ........................... 435/158 |
| 5,096,820 | 3/1992 | Leleu et al. | |
| 5,238,826 | 8/1993 | Leleu et al. | |
| 5,563,303 | * 10/1996 | Vuorinen | ..................... 568/864 |
| 5,714,602 | * 2/1998 | Beck et al. | |
| 5,739,303 | * 4/1998 | Beck et al. | |

FOREIGN PATENT DOCUMENTS

| | | |
|---|---|---|
| EP | 8505912 | * 10/1985 |
| EP | 0 403 392 | 12/1990 |
| EP | 0 421 882 | 4/1991 |
| GB | 1 233 146 | 5/1971 |
| WO | 93/19030 | 9/1993 |
| WO | 94/10325 | 5/1994 |
| WO | 95/02967 | 2/1995 |

OTHER PUBLICATIONS

Journal of Fermentation Bioengineerng, vol. 70, No. 4, 1990 Amsterdam, NL pp. 228–231, XP 000565376 J.Escalante, et al: "production of arabitol from glucose by hansenula polymorpha".

Patent Absract of Japan, vol. 11 No. 307 (C–450), Oct. 7, 1987 & JP–A–62 096090 (National Food Research Institute) May 2, 1987.

Chemical Abstracts, vol 77, No. 13, Sep. 25, 1972, Columbus, Ohio,US; abstract No. 86674X, p. 306 *abstract* & JP–A–48 013 707 (noda institute for scientific research) Apr. 25, 1972.

Journal of the Chemical Society, Chemical Communications, No. 18, Sep. 15, 1988 Letchworth, GB, pp. 1266–1267,M.A.Andrews, et al: Decardonylation of sugars by chlorotris (triphenylphosphine)–rhodium.

Applied Microbiology, vol. 8, No. 6, Dec. 1969 Washington, DC,US, pp. 1031–1035.XP 000565389 H.Onishi et al: "Microbial Production of xylitol from glucose".

* cited by examiner

Primary Examiner—Christopher R. Tate
(74) Attorney, Agent, or Firm—Fitch, Even, Tabin & Flannery

(57) ABSTRACT

The present invention relates to a process for the production of xylitol. Specifically the process comprises two reaction steps. The first step is the fermentative conversion of a hexose to a pentitol. The second step is the catalytic chemical isomerisation of the pentitol to xylitol. Optionally, the xylitol is separated from the other pentitols.

11 Claims, No Drawings

PROCESS FOR THE PRODUCTION OF XYLITOL

The present invention discloses a method for producing a pentitol. The present invention relates to a method for producing pentitols from hexoses. Specifically, xylitol is obtained from glucose in a reaction comprising a sequence of only two separate steps. Glucose is fermented to arabinitol and chemically isomerised to a pentitol mixture comprising xylitol.

Xylitol is produced on an industrial scale by hydrogenation of xylose. Xylose is not available as such it is obtained from xylan-containing plant materials. In order to obtain xylose, xylan-containing plant materials such as almond shells, corn cobs or birch wood are hydrolysed in acidic medium at elevated temperatures. This hydrolysis suffers from two major disadvantages: a high load of waste material due to the low content of xylan in the above mentioned starting materials and a low product purity and yield due to considerable formation of by-products under the extreme hydrolysis conditions which are used. Extensive purification and refining is required to remove excess of acid and the pronounced colour. The subsequent crystallisation of the demineralised xylose syrup suffers from the low purity of the xylose syrup. Other hemicellulosic sugars also formed during hydrolysis have similar physico-chemical properties and have to be removed quantitatively. In an earlier stage to avoid the formation of galactitol, galactose has to be removed prior to the catalytic hydrogenation. Application of xylitol in food and related products requires the complete removal of galactitol for reasons of human safety, e.g. eye damage.

For every kilogram of crystalline xylitol 12 to 13 kg of almond shells have to be processed, resulting in about 11 to 12 kg of solid waste. Apart from a pollution problem there is also a logistic problem with this process in that large quantities of almond shells have to be transported. Finally, the availability of the xylan containing material may become a limiting factor.

It is therefore of interest to consider alternative processes for producing xylitol which do not suffer from the mentioned drawbacks. Chemical and microbial processes for producing xylitol have been described.

Recently, some reaction schemes to produce xylitol, starting from readily available hexoses, in particular D-glucose and D-galactose, have been published. All of these schemes comprise a sequence of more than two reaction steps. In a first step the hexose is submitted to a chain shortening reaction which yields a $C_5$-intermediate. This step is performed either fermentatively or chemically. The subsequent process relates to the conversion of the $C_5$-intermediate into xylitol, by using a sequence of at least two fermentative and/or chemical conversion steps.

In EP 403 392 and EP 421 882 a four step process is disclosed in which glucose is fermented to D-arabinitol by an osmophilic yeast. Subsequently, the arabinitol ($C_5$-intermediate) is converted by bacteria (Acetobacter, Gluconobacter or Klebsiella) into D-xylulose. In the third step xylulose is isomerised by glucose (xylose) isomerase into a xylose/xylulose mixture. In the final step either the xylose is enriched prior to hydrogenation by chromatography, or the xylulose/xylose mixture is directly subjected to hydrogenation followed by the separation of xylitol by chromatography.

In WO 93/19030 glucose, fructose or galactose or mixtures thereof (obtained by hydrolysis of the disaccharides sucrose and lactose) are oxidatively decarboxylated into alkali metal arabinonate and lyxonate, respectively. These intermediates are first converted to the aldonic acid form. Subsequently, the aldonic acids which are the $C_5$-intermediates, are transformed into xylitol. When L-sorbose is used, L-xylonate is obtained via the oxidative decarboxylation and this is converted to the aldonic acid form before being hydrogenated to xylitol. This last pathway seems simple however one has to take into account the reaction steps required to obtain L-sorbose. L-Sorbose is mainly obtained via fermentative oxidation of sorbitol, which in turn is obtained from glucose by catalytic hydrogenation, resulting overall in five reaction steps to obtain the final xylitol.

Other chemical methods for xylitol preparation include elaborated reaction schemes involving the use of protection groups. Due to the lack of economic feasibility these reactions are not further considered here (Helv. Chim. Acta 58, 1975, 311).

Several exclusively microbiological pathways have been published, however, none of them are competitive because of the overall yield which is far too low.

There exists therefore a need for an economically valuable method for producing pentitols, especially xylitol, with a low level of impurities, which is easily refinable, which comprises a short reaction sequence, and starting from readily available hexoses, such as glucose (anhydrous, monohydrate, or high dextrose syrups).

The present invention provides such a method. The present invention relates to a method for producing a pentitol from a hexose characterised in that the method comprises the following steps,
a) fermentation of a hexose to yield a C5-intermediate consisting mainly of a pentitol,
b) isomerisation of the pentitol of step a) in the presence of a chemical catalyst to yield a corresponding pentitol mixture,
c) optionally separation of the desired pentitol from the product of step b).

The present invention can be summarised as follows. The invention discloses the fermentation of $C_6$-carbohydrates which results in $C_5$-polyols, the fermentation step is followed by chemical catalytic isomerisation. The starting material can be any easily available $C_6$-carbohydrate, the preferred substrate is glucose, anhydous as monohydrate or in the form of a high dextrose syrup. Starting with glucose the fermentation yields mainly arabinitol. The fermentation of the present invention is based on methods known in the art. In carrying out a process according to the present invention, any yeast which has an ability to produce D-arabinitol from glucose may be used. For example yeasts belonging to the genera Pichia, Endomycopsis, Hansenula, Debarvomyces, Zygosaccharomyces, Saccharomyces, Candida and other yeasts belonging to the genus Torulopsis are suitable for this particular fermentation.

The yield of D-arabinitol in the fermentation product is preferably larger than 20% (w/w) more preferably larger than 40% (w/w) based on the initial hexose content. In general with the use of osmophylic yeasts D-arabinitol is the only pentitol which is produced.

The D-arabinitol is subjected to catalytic isomerisation by methods known in the art. D-arabinitol is treated at temperatures between 70 and 250° C., preferably at a temperature above 100° C., and at hydrogen gas pressures between 0.1 and 10 MPa, preferably between 1 and 8 MPa.

The catalytic isomerisation is performed in the presence of catalysts which are known in the art for perfoming hydrogenation/dehydrogenation. Suitable catalysts include ruthenium, copper, palladium, platinum, rhodium, cobalt and nickel based catalysts, or their oxides and mixtures thereof.

The polyol isomerisation is performed at distinctly different pH levels, and the addition of alkali or acid has an influence on the thermodynamic equilibrium of the pentitol mixture. The isomerisation reaction results in a product containing xylitol, ribitol and DL-arabinitol. Xylitol is present in these mixtures in more than 10% preferably in more than 20%. The reaction product further contains some lower alditols, such as tetritols and triitols, adding up to a maximum of 10% preferably only to 5% of the total alditol content.

The isomerisation mixture is optionally subjected to chromatography on cationic resin material yielding purified xylitol with a purity in excess of 95%. Preferably the mixture is first demineralized and subsequently submitted to chromatography. The refining is suitably performed using a strong cation exchange resin e.g. Duolite C 26 followed by a medium base anion exchange resin Duolite A 368. This process is preferably repeated once. On industrial scale chromatography is performed using suitable equipment obtainable for example from Mitsubishi with Diaion UBK-555 resin (in $Ca^{2+}$ form).

The other pentitols are optionally recycled to the polyol isomerisation step, resulting in increased overall yield. The xylitol can also be further purified by crystallisation.

The advantage of this process in comparison with earlier described processes such as the process disclosed in WO 93/19030 is that well established unit operations can be used for the refining (classical syrup refining) and that known techniques and equipment for fermentation and catalytic isomerisation can be used. The main advantage compared with other methods such as described in EP 403 392 and EP 421 882 and WO 93/19030 is the much shorter overall reaction sequence. Schematically the method of the present invention is illustrated in Scheme 1, wherein the underlined steps are essential.

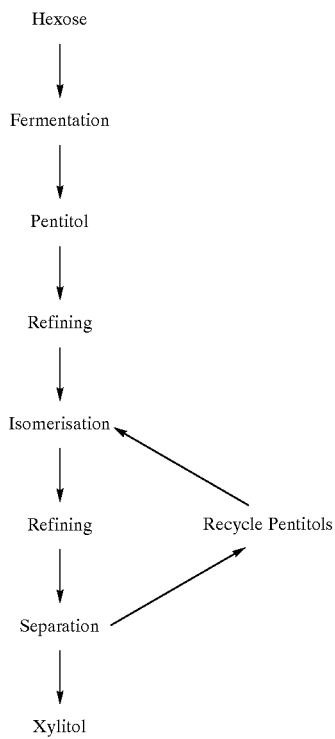

Scheme 1

The invention is further illustrated by the following examples.

EXAMPLE 1

Zygosaccharomyces barkeri Y-222 is inoculated in a culture medium containing 30% (w/v) glucose, 4.0% (w/v) corn steep liquor, 0.1% (w/v) potassium phosphate, 0.05% (w/v) magnesium sulphate, 0.01% (w/v) calcium chloride, 0.01% (w/v) sodium chloride, and cultured at pH 6, (pH-adjustment with sodium hydroxide) at 30° C. for 4 days. The following yield is obtained: 46.1% arabinitol, 2% residual glucose, and 10.5% glycerol (as a percentage of glucose which has been converted). The reaction product is demineralized and refined on a double-pass ion exchange battery, followed by selective crystallisation of the arabinitol. This results in crystals with a purity of 99%.

Arabinitol was isomerised on ruthenium catalyst (4% catalyst on total dry substance), which is supported on silica (5% Ru on silica), by applying a hydrogen pressure of 4 MPa at a temperature of 150° C. Polyol isomerisation is completed within 4 hours. The obtained demineralized isomerisate has the following pentitol composition: arabinitol (60%), xylitol (22%), ribitol (18%).

The xylitol was separated by chromatography on cation exchange resin in the calcium form, yielding xylitol with a purity greater than 95%. The arabinitol and ribitol were recycled to isomerisation. The xylitol was crystallised to obtain crystals of 99.9% purity.

EXAMPLE 2

Pichia ohmeri ATCC 20.209 was cultured at 30° C. in a medium containing 15% (w/v) glucose, 0.2% (w/v) yeast extract, 0.1% (w/v) potassium hydrogen phosphate and 0.1% (w/v) magnesium sulphate. After 6 days the reaction medium was filtered and demineralized on ion exchange resins. A yield of 40.5% arabinitol was obtained, after crystallisation.

Arabinitol was isomerised on ruthenium catalyst (6% catalyst on total dry substance), which is supported on active carbon (5% Ru on carbon). To isomerize the arabinitol syrup phosphoric acid (1% on total dry substance) was added. The reaction temperature was 150° C. at a hydrogen pressure of 4 MPa. Within 4 hours the isomerised syrup had the following composition: 90% total pentitols (of which: arabinitol (45%), xylitol (34%), ribitol (21%)) and 10% lower alditols.

The xylitol was recovered in a similar way as described in example 1.

EXAMPLE 3

Fermentation of glucose to arabinitol is performed by using a culture medium of 10% (w/v) glucose, 0.5% (w/v) yeast extract and 0.1% (w/v) urea. The medium is inoculated with a yeast strain of the genus *Endomycopsis chodati*. After 72 hours fermentation time 56% arabinitol was obtained without considerable amounts of glycerol (below 4%). After demineralisation and refining the arabinitol syrup is directly used for polyol isomerisation in the presence of Raney-nickel (5% catalyst slurry on total dry substance). The pH is increased to 11, by the addition of 0.5 M NaOH. A hydrogen pressure of 4 MPa is applied at a temperature of 170° C. and the isomerisation reaction is stopped after 4 hours, resulting in a pentitol mixture of the following composition: arabinitol (90%), xylitol (6%), ribitol (4%).

EXAMPLE 4

Fermentation of glucose to arabinitol is performed as described in example 1, except that a yeast strain belonging to the genus Candida, namely *Candida polymorpha* ATCC 20 213 is used. 4.5 g of D-arabinitol was obtained per 100 ml fermentation liquor. The subsequent polyol isomerisation is performed on a ruthenium catalyst (4% catalyst on total dry substance) which is supported on zeolite material (5% Ru on zeolite). The reaction temperature is 135° C. at a hydrogen pressure of 4 MPa. After 4 hours reaction the polyol mixture has the following pentitol composition: arabinitol (73%), xylitol (13%), ribitol (14%).

The xylitol is recovered as in example 1.

What is claimed is:

1. A method for producing xylitol from glucose which is in anhydrous, monohydrate or high glucose syrup form, said method comprising:

(a) fermenting said glucose to yield mainly arabinitol, (b) isomerizing said arabinitol in the presence of a hydrogenation/dehydrogenation catalyst and a catalyst promoter comprised of phosphoric acid, to yield a corresponding pentitol mixture containing xylitol, and, optionally, (c) separating said xylitol from said pentitol mixture.

2. A method according to claim 1, wherein said method includes step (c), and said separating comprises using a cation resin in obtaining xylitol from said pentitol mixture.

3. A method according to claim 1, wherein said arabinitol is refined after said fermenting.

4. A method according to claim 1, wherein in said fermenting is an aerobic fermentation of said glucose syrup to arabinitol using an osmophilic yeast selected from the group consisting of the following genera: Endomycopsis, Hansenula, Debaryomyces, Zygosaccahromyces, Saccharomyces, Candida and Torulopsis.

5. A method according to claim 1, 2, 3, or 4 wherein said isomerizing is conducted under hydrogen at a hydrogen pressure between 0.1 and 10 Mpa and a temperature between 70° C. and 250° C.

6. A method according to claim 5, wherein the hydrogen pressure is between 1 and 8 Mpa.

7. A method according to claim 5, wherein the temperature is between 100 and 200° C.

8. A method according to claim 1, wherein said fermenting comprises aerobicly fermenting said glucose syrup to arabinitol using an osmophilic yeast from the genus Pichia.

9. A method according to claim 1, wherein said method comprises steps (a), (b) and (c).

10. A method according to claim 9, wherein a residual pentitol mixture is obtained after (c), and said residual pentitol mixture is recycled to step (b).

11. A method for producing xylitol from glucose, wherein said glucose is in anhydrous, monohydrate, or glucose syrup form, said method comprising:

(a) fermenting said glucose to obtain a reaction product including arabinitol;

(b) optionally demineralizing said reaction product;

(c) isomerizing said arbitinol to yield a corresponding pentitol mixture that contains xylitol, said isomerizing being conducted in the presence of a hydrogenation/dehydrogenation catalyst and wherein the isomerization equilibrium is shifted towards the desired xylitol through the additions of an inorganic acid comprising phosphonic acid; and (d) separating said xylitol from said pentitol mixture.

* * * * *